United States Patent
Cronin et al.

(10) Patent No.: US 10,820,843 B2
(45) Date of Patent: Nov. 3, 2020

(54) MODULAR MONITORING DEVICE PLATFORM WITH INTERCHANGEABLE MODULES

(71) Applicant: KONINKLIJKE PHILIPS N.V., Eindhoven (NL)

(72) Inventors: John E. Cronin, Bonita Springs, FL (US); Christopher Michael Huffines, Bonita Springs, FL (US)

(73) Assignee: Koninklijke Philips N.V., Eindhoven (NL)

(*) Notice: Subject to any disclaimer, the term of this patent is extended or adjusted under 35 U.S.C. 154(b) by 116 days.

(21) Appl. No.: 15/761,189

(22) PCT Filed: Sep. 22, 2016

(86) PCT No.: PCT/EP2016/072517
§ 371 (c)(1),
(2) Date: Mar. 19, 2018

(87) PCT Pub. No.: WO2017/050878
PCT Pub. Date: Mar. 30, 2017

(65) Prior Publication Data
US 2018/0263542 A1 Sep. 20, 2018

Related U.S. Application Data

(60) Provisional application No. 62/222,665, filed on Sep. 23, 2015.

(30) Foreign Application Priority Data

Mar. 18, 2016 (EP) .................................. 16161221

(51) Int. Cl.
*A61B 5/1455* (2006.01)
*A61B 5/00* (2006.01)
(Continued)

(52) U.S. Cl.
CPC ........ *A61B 5/14551* (2013.01); *A61B 5/0022* (2013.01); *A61B 5/02055* (2013.01);
(Continued)

(58) Field of Classification Search
None
See application file for complete search history.

(56) References Cited

U.S. PATENT DOCUMENTS

| 4,325,385 A | 4/1982 | Holte |
| 5,590,648 A | 1/1997 | Mitchell |
| (Continued) | | |

FOREIGN PATENT DOCUMENTS

| CN | 104434061 A | 3/2015 |
| EP | 2898822 | 7/2015 |

OTHER PUBLICATIONS

Sung, et al., "Wearable feedback systems for rehabilitation"; J Neuroengineering Rehabil. 2005; 2: 17.
(Continued)

*Primary Examiner* — Eric F Winakur
*Assistant Examiner* — Marjan Fardanesh

(57) ABSTRACT

Systems and methods for operating a modular pulse oximeter platform with interchangeable modules. The method comprises selecting a plurality of modules based on a health context and connecting in a serial manner the plurality of modules and a pulse oximeter platform via a plurality of connection means. The pulse oximeter interprets identification numbers from the plurality modules and operates the connected plurality of modules accordingly. Data received from the plurality of modules are associated with each other or with pulse oximeter data.

10 Claims, 8 Drawing Sheets

(51) Int. Cl.
  *A61B 5/0205* (2006.01)
  *G16H 40/67* (2018.01)
  *G06F 19/00* (2018.01)
  *G16H 40/63* (2018.01)

(52) U.S. Cl.
  CPC .............. *G06F 19/00* (2013.01); *G16H 40/63* (2018.01); *G16H 40/67* (2018.01); *A61B 2560/045* (2013.01); *A61B 2562/08* (2013.01); *A61B 2562/227* (2013.01)

(56) References Cited

U.S. PATENT DOCUMENTS

| | | |
|---|---|---|
| 7,230,688 B1 | 6/2007 | Villarreal |
| 8,253,586 B1 | 8/2012 | Matak |
| 2005/0075067 A1 | 4/2005 | Lawson |
| 2005/0148832 A1 | 7/2005 | Reghabi |
| 2006/0122466 A1 | 6/2006 | Nguyen-Dobinsky |
| 2007/0088249 A1 | 4/2007 | Duffy |
| 2007/0140964 A1 | 6/2007 | Sprecher |
| 2010/0005117 A1 | 1/2010 | Stut |
| 2010/0156676 A1 | 6/2010 | Mooring |
| 2012/0029304 A1 | 2/2012 | Medina |
| 2012/0185267 A1 | 7/2012 | Kamen |
| 2012/0311219 A1 | 12/2012 | Ma |
| 2015/0157220 A1 | 6/2015 | Fish |

OTHER PUBLICATIONS

GE, CARESCAPE Monitor B650, product information, Jul. 22, 2015.

Dezeen, "Healthmonitoring components designed for Google's Project Ara modular smartphone"; Jan. 22, 2015.

| ID Signal Number | Module Type |
|---|---|
| 0154873 | TK 427 Pulse Oximeter |
| 0154874 | T-16 Memory |
| 0154875 | BTL-S3 Controller (Universal) |
| 0154876 | BTL-S3 Controller (Universal) |
| 0154877 | BTL-S3 Controller (Universal) |
| 0154878 | TK 427 Pulse Oximeter |
| 0154879 | T-16 Memory |
| 0154880 | BTL-A4 Controller (Bed) |
| 0154881 | T65C GPS |
| ... | |

FIG. 7

| Module Type | Data Files |
|---|---|
| BTL-A4 Controller (Bed) | BTLmain.dat, A4DisplayDriver.dat, A4GUI.dat |
| BTL-S3 Controller (Universal) | BTLmain.dat, S3ButtonController.dat |
| TK 427 Pulse Oximeter | TK427sensor.dat, TK427OffPostDetection,dat, TK427PIcalculator.dat |
| T-16 Memory | T16InputOutput.dat, T16indexing.exe, T16compression.exe |
| T65C GPS | T65CReceiver.dat, T65CAlgorithms.dat |
| ... | |

FIG. 8

MODULAR MONITORING DEVICE PLATFORM WITH INTERCHANGEABLE MODULES

CROSS REFERENCE TO RELATED APPLICATIONS

This application is the U.S. National Phase application under 35 U.S.C. § 371 of International Application No. PCT/EP2016/072517, filed Sep. 22, 2016, published as WO 2017/050878 on Mar. 30, 2017, which claims the benefit of European Patent Application Number 16161221.3 filed Mar. 18, 2016 and U.S. Provisional Patent Application No. 62/222,665 filed Sep. 23, 2015. These applications are hereby incorporated by reference herein.

BACKGROUND OF THE INVENTION

Modular devices are known wherein multiple modules may be incorporated to extend the functionality of a base device. Modularity provides an advantage in extending the usability of a device as it reduces the need to replace an old device with a newer device having better functionalities. Instead, new modules can be purchased and incorporated into the base device. Modularity also provides flexibility and adaptability as various modules may be selected based on the context. Necessary modules can be selected while modules no longer needed or wanted can be removed from the modular device platform with ease. Modularity is particularly advantageous in the health industry, such as in hospitals, clinics, emergency rooms, doctor's offices, and long-term home care facilities. As there is diversity in patient condition and health context, there is also a variety of ways in combining medical devices suited for a particular patient condition or health context.

SUMMARY OF THE CLAIMED INVENTION

Embodiments according to the present invention relates to systems and methods for operating a modular pulse oximeter platform with interchangeable modules. The system comprises a pulse oximeter as the platform for connecting a plurality of modules selected based on a health context. Each of the plurality of modules and the pulse oximeter comprises a plurality of connection means for mechanically, electronically, and electrically connecting in a serial manner the pulse oximeter to the plurality of modules.

The method according to some embodiments comprises connecting in a serial manner a pulse oximeter and a plurality of modules selected based on a health context via a plurality of connection means. The plurality of modules are identified and operated in proximity to a single body part. Afterwards, the pulse oximeter retrieves and associates the various module data and pulse oximeter data.

BRIEF DESCRIPTION OF THE DRAWINGS

FIG. 7 is an illustrative embodiment of the ID database according to an embodiment of the present invention.

FIG. 8 is an illustrative embodiment of the module program database according to an embodiment of the present invention.

DETAILED DESCRIPTION OF THE EMBODIMENTS

Figure 1:
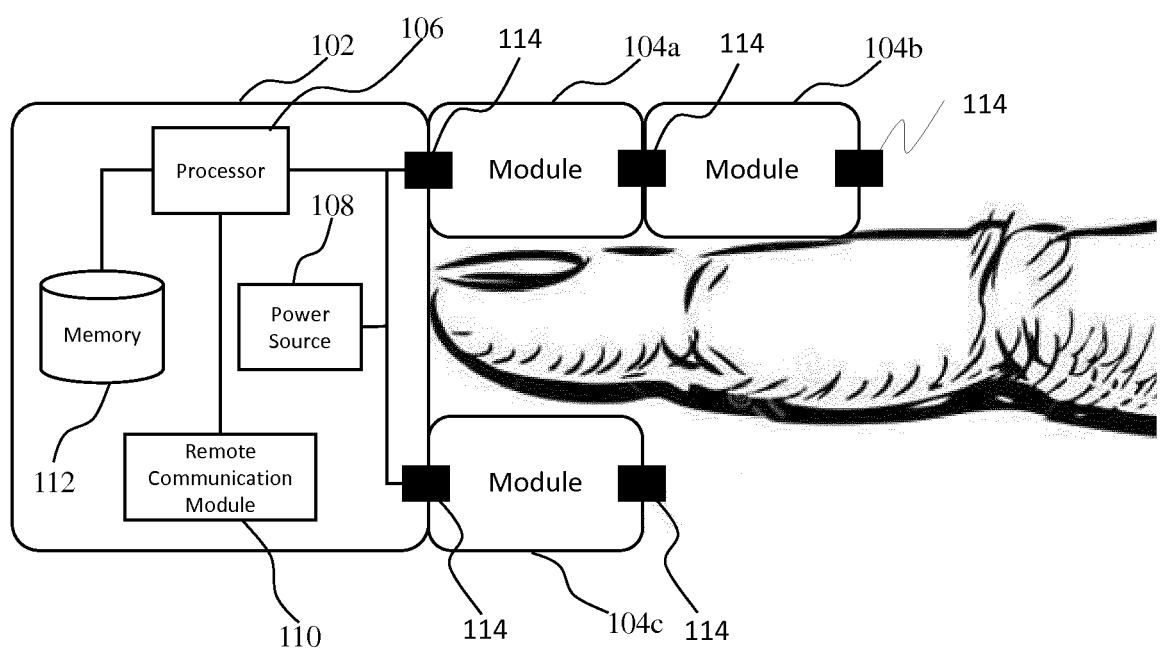
FIG. 1 illustrates a block diagram of a system for operating a modular pulse oximeter platform with interchangeable modules according to a preferred embodiment of the present invention.

Some embodiment of the present invention relates to a method for operating a modular pulse oximeter platform with interchangeable modules comprising: connecting in a serial manner a pulse oximeter and a plurality of modules selected based on a health context via a plurality of connection means; identifying a plurality of identification numbers transmitted by the plurality of modules; operating via a pulse oximeter processor the pulse oximeter and the plurality of modules in proximity to a single body part; transmitting module data from the plurality of modules to the pulse oximeter; and associating at least two of the plurality of transmitted module data and pulse oximeter data.

Some embodiment of the present invention also relates to a modular pulse oximeter platform 100 with interchangeable modules 104 (e.g., 104a-104c) comprising a pulse oximeter 102 including a power source 108 and a remote communication module 110, and a plurality of modules 104 (e.g., 104a-104c) each having an active subunit, wherein each of the pulse oximeter and the plurality of modules has its processor (e.g., 106, 204), memory (e.g., 112, 206) and connection means 114 for mechanically, electronically, and electrically connecting in a serial manner the pulse oximeter and the plurality of modules.

Figure 2:
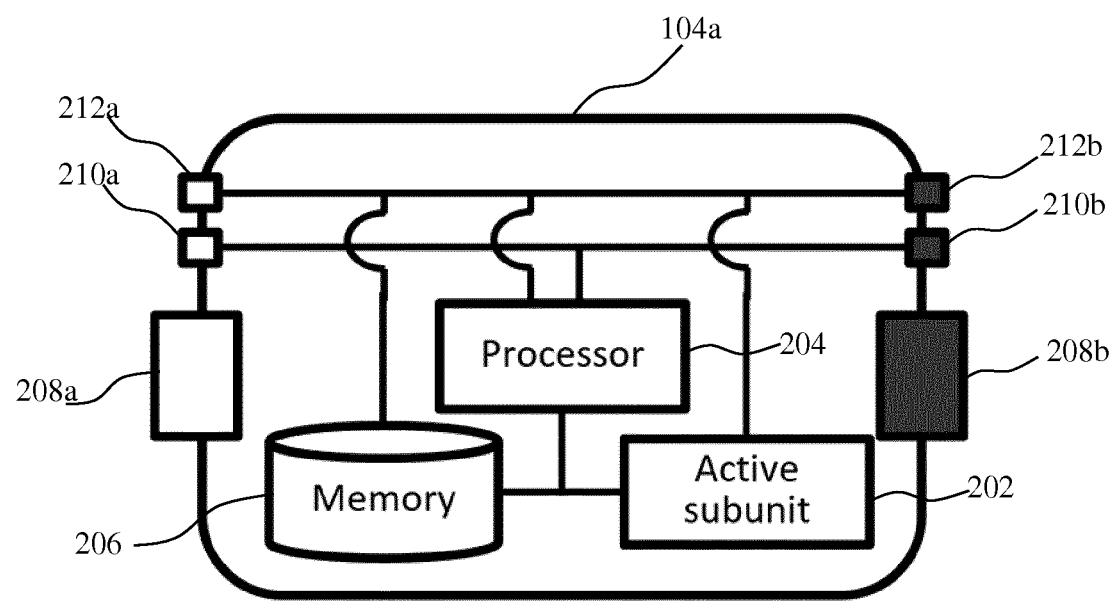
FIG. 2 is a block diagram of a module according to a preferred embodiment of the present invention.

In a preferred embodiment illustrated in FIG. 1, a pulse oximeter 102 is provided as a monitoring platform to which a plurality of modules 104a-c are serially connected. The pulse oximeter 102 comprises a processor 106, a power source 108, a remote communication means 110, a memory module 112, and a plurality of connection means 114. An exemplary embodiment of the module 104a illustrated in FIG. 2 comprises an active subunit 202, a processor 204, a memory module 206, and a plurality of connection means 208a, 208b, 210a, 210b, 212a, and 212b for mechanically, electronically, and electrically connecting the module 104a to either the pulse oximeter 102 or to the module 104b. In the connected serial configuration, the mechanical connection means 208a mechanically interlocks the module 104a to the pulse oximeter 102 while mechanical connection means 208b mechanically interlocks the module 104a to the module 104b. In the same configuration, the power communication means 210a enables the supply of power from the power source 108 to the module 104a, while the power communication means 210b enables the supply of power to the module 104b. In the same connected serial configuration, the data connection means 212a and 212b also enable the communication of data among the pulse oximeter 102 and the plurality of module 104a-c by connecting the plurality of data communication means 212a and 212b of each module 104a-c to the pulse oximeter 102.

The pulse oximeter 102 is preferably a portable pulse oximeter device adapted to be worn on a patient's finger and adapted to measure the oxygen saturation of the patient. Alternatively, the pulse oximeter 102 is adapted to be clipped onto the patient's ear, toe, or a body part other than the patient's finger.

A plurality of modules 104a-c are selected based on a health context of the patient and are serially connected to the pulse oximeter 102. The modular design of some embodiments of the present invention enables the interchangeability and customizability of modules 104a-c as needed based on the health context. Any number of modules can be connected in series to the pulse oximeter 102. Further, the operation of the modular pulse oximeter platform is preferably independent of the sequence in which the modules are attached. For example, a first configuration having the sequence that includes a temperature module, a blood pressure module, and a microphone module preferably functions in the same manner as a second configuration having the sequence that includes a blood pressure module, a microphone module, and a blood pressure module. Modules 104a-c may perform various functions, and they include modules for measuring temperature (temperature module), determining location using Global Positioning Satellite signals (GPS module), emit a security alert when moved into or out of a specific location (security alert module), may contain a barcode or other identification means (ID module), an accelerometer (accelerometer module), or may measure chemical detectors using microelectromechanical systems, reagent strips, or other means (chemical detection module).

In another embodiment, the pulse oximeter comprises more than one connection means for attaching more than one series of modules. For example, the pulse oximeter 102 illustrated in FIG. 1 has two connection means 114 to which two modules 104a and 104c may be connected to the pulse oximeter 102 in a parallel manner. Additional electronic modules may be connected in a serial manner to either module 104a or module 104c.

The health context may be, for example, a disease, a symptom, ambient conditions, patient age, or a specific situation. Customization is performed by the user or a medical professional by considering the health context and the data desired for acquisition. For example, a patient experiencing difficulty in breathing will be monitored by customizing the pulse oximeter with a blood pressure module, a temperature module, an SD card module, a Bluetooth sensor module, and a microphone module.

The serial manner by which the pulse oximeter 102 and the plurality of modules 104a-c are connected with each other is enabled by the plurality of connection means 208a, 208b, 210a, 210b, 212a, and 212b, which may be tongue and groove elements or male and female connectors wherein a first connection means is located on one side of the module or the pulse oximeter and a second connection means is located on an opposite side of the module or the pulse oximeter, such that stacking or connecting two modules will cause the first connection means and the second connection means to be mechanically interlocked. In an exemplary embodiment, the connection means 208a, 210a, and 212a are female connectors, while the connection means 208b, 210b, and 212b are male connectors, wherein the male connectors 208a, 210a, and 212a of the module 104a are adapted to be received by the female connector 208b, 210b, and 212b of a second module.

The active subunit 202 residing inside each of the plurality of modules 104a-c is preferably a physiological sensor for measuring a physiological parameter of a user (e.g., the patient), such as respiration, pulse, blood pressure, temperature, and pH. The active subunit 202 may also be any module element such as an actuator, tactile stimulator, controller, memory card, Bluetooth adapter, or any module that extends the functionality of the pulse oximeter 102.

Figure 3:
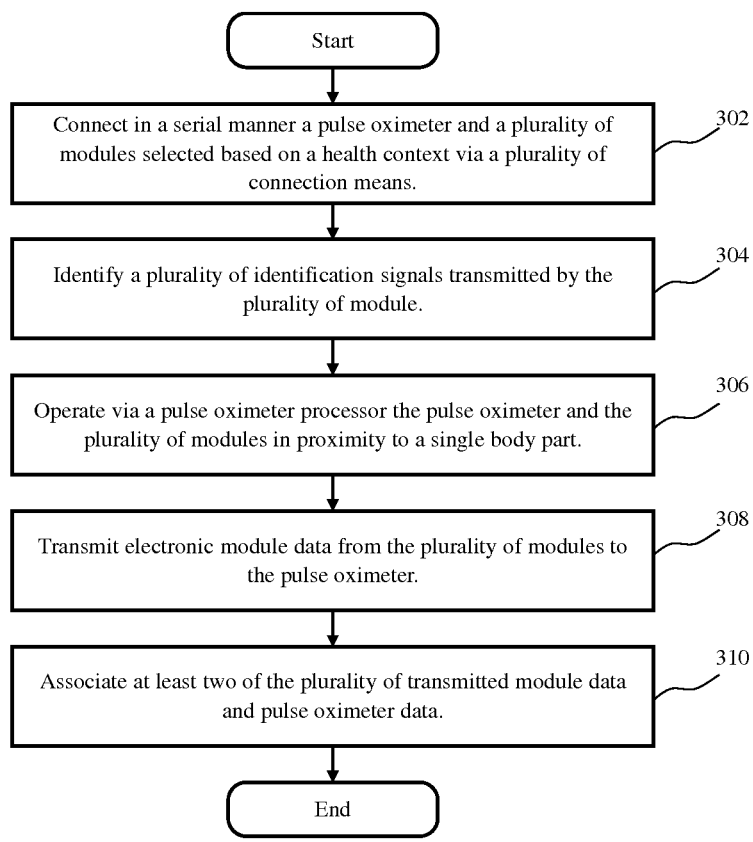
FIG. 3 is a flowchart of a preferred method of the present invention.

FIG. 3 illustrates a preferred method of the present invention. A plurality of modules 104 are selected based on a health context and the selected plurality of modules 104 are then connected with each other and to a pulse oximeter 102 in a serial manner via a plurality of connection means 114 (step 302). Identification (ID) numbers are transmitted by the modules 104 and upon receipt by the pulse oximeter 102, the ID numbers are identified (step 304). These ID numbers may be transmitted by wired or wireless means. Based on the ID numbers, the pulse oximeter processor 106 operates the connected modules 104 accordingly using software and rules configured for the ID numbers (step 306). The physical dimensions and the serial configuration of the pulse oximeter 102 and the plurality of modules 104 enable the operation of the pulse oximeter 102 and the plurality of modules 104 in proximity to a single body part, e.g., the patient's right hand, the patient's right ear, or the patient's left foot. Data, such as sensor data acquired by a sensing module, is communicated between the modules 104 and the pulse oximeter 102 (step 308). The various sets of data obtained by the pulse oximeter processor 106 from the pulse oximeter 102 and the plurality of modules 104 are associated with each other using analytical tools and algorithms (step 310).

In accordance with an embodiment of the present invention, the step of associating at least two of the plurality of transmitted module data and pulse oximeter data (i.e., the step of associating the various data) involves the synchronization, correlation, and computation of respective data sets. Data obtained from the pulse oximeter 102 and the plurality of modules 104 are time-stamped and grouped together. For example, pulse oximeter 102, temperature data and blood pressure data obtained during one session will be tagged as belonging to the same patient and to the same session. Alternatively, the step of associating the various data sets comprises inputting the various data sets to an algorithm to perform functions such as calibration, correlation, and diagnosis.

In one exemplary embodiment of the present invention, a medical professional monitors the vital signs of a patient. The medical professional selects modules customized to the patient. Thus, the medical professional may connect a temperature sensor, a blood pressure sensor, an SD card module, a display module, and a microphone to a pulse oximeter platform. The connected modules 104 are identified by the pulse oximeter 102 and are operated according to predefined operational parameters, e.g., module driver, sampling frequency, and memory allocation. Data obtained by the temperature sensor, the blood pressure sensor, and the microphone are sent to the pulse oximeter, wherein the pulse oximeter processor groups the temperature data, blood pressure data, and audio data into a data set associated with the session and/or patient. Following these steps, the medical professional may remove the display module and attach a Wi-Fi module, so that these data can be uploaded to a cloud server for further processing.

Figure 4:
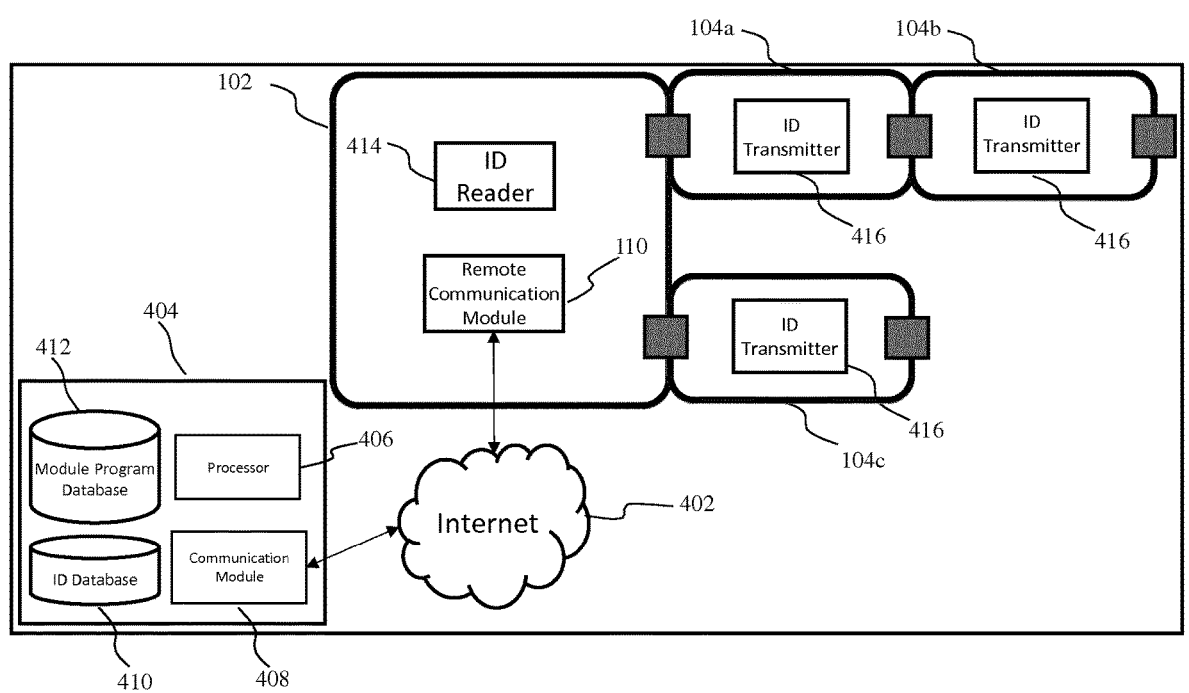
FIG. 4 is a block diagram of a modular pulse oximeter platform connected to a health network according to an embodiment of the present invention.

In another embodiment of the present invention illustrated in FIG. 4, the pulse oximeter 102 connects to the internet 402 using the remote communication module 110 in order to communicate with a health network 404 comprising a health network processor 406, a communication module 408, an ID database 410, and a module program database 412. In this embodiment, the pulse oximeter 102 houses an ID reader 414, while each of the modules 104a-c houses an ID transmitter 416 for transmitting ID numbers where each ID number uniquely identifies the respective module. The ID reader 414 and ID transmitter 416 are wireless communication modules adapted for RFID, Bluetooth, Wi-Fi, cellular communication, or other wireless communication technology. Alternatively, the ID reader 414 and the ID transmitter 416 are software functions performed by the processors of the pulse oximeter and the plurality of modules, respectively, and the ID number is communicated via the plurality of communication means described herein.

The ID database 410 according to an embodiment of the present invention is a database that stores ID numbers and corresponding module types. As used herein, the term "module type" refers to the type of module based on, for example, their specific functionalities, e.g., a module that functions as a controller or a temperature sensor. A module type may also include information relating to the brand, model, manufacturing information, or any information identifying the module. The module program database 412 according to an embodiment of the present invention stores in a table form the various module types and program data files necessary to operate the module type. The various programs necessary to run the individual modules or a combination of modules include device drivers, configuration files, settings data, user profiles, or any routine, program, object, component, data structure, etc. to perform particular tasks.

In one embodiment of the present invention, the health network 404 is a cloud service network for providing programs necessary to operate the plurality of modules. The health network 404 may be any network managed by a manufacturer, a third party cloud service provider, a government agency, a hospital, or a local area network computer, for example.

Figure 5:
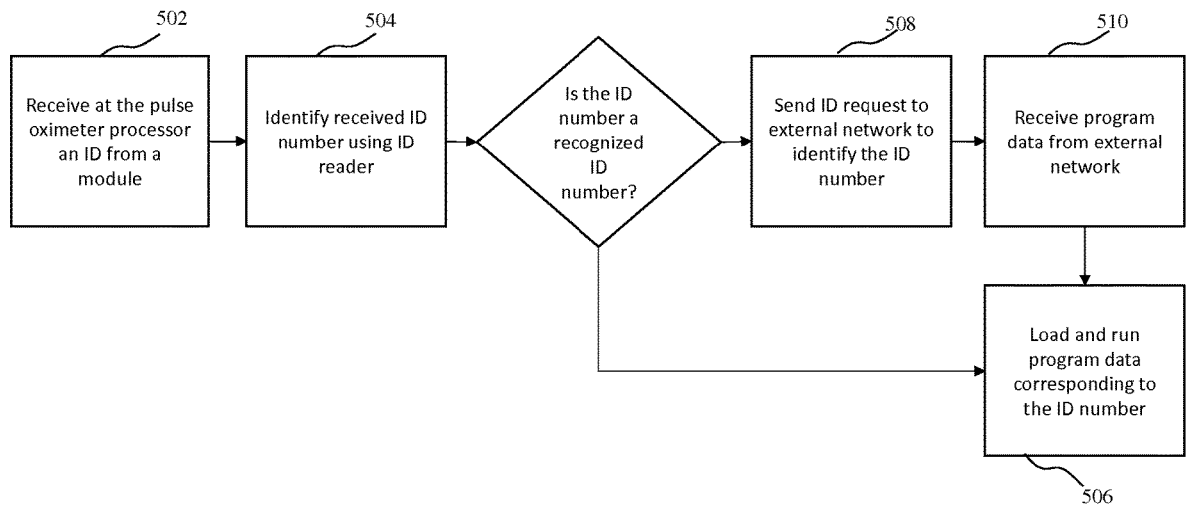
FIG. 5 is a flowchart of modular pulse oximeter platform software according to an embodiment of the present invention.

FIG. 5 is a flowchart that shows the algorithm executed by the pulse oximeter processor 106 or the processor 204, or both. Upon connection of an at least one module 104 to the pulse oximeter 102, the pulse oximeter processor 106 receives the ID number(s) transmitted by the connected module (step 502). Thereafter, the ID reader 414 is activated in order to identify the ID number(s) (step 504). If the ID number is identified, program data corresponding to the ID number are loaded and run (step 506) such that the connected module(s) 104 are enabled to perform one or more corresponding functions. Some or all of the program data may be loaded and run by the pulse oximeter processor 106, the processor 204, or a combination of the pulse oximeter processor 106 and one or more processors 204. If the ID number is not recognized, an ID request that includes the unrecognized ID number is sent using the pulse oximeter 102's remote communication module 110 to a health network 404 (step 508). After identification by the health network 404, the necessary programs are received by the pulse oximeter 102 (step 510).

Figure 6:
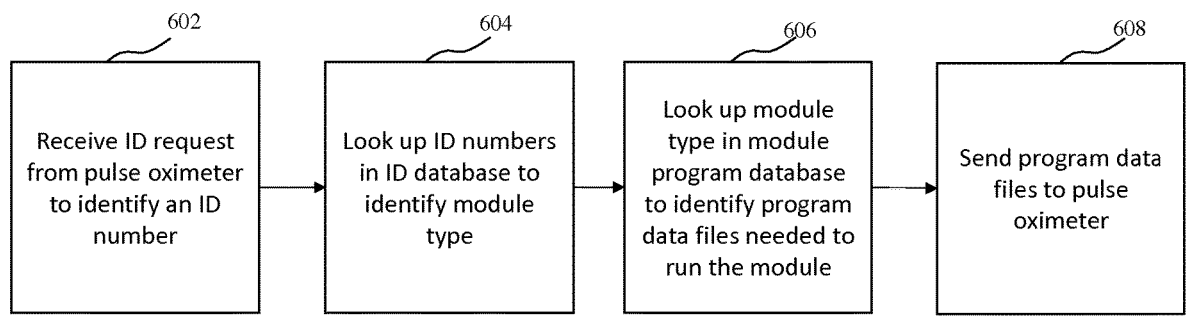
FIG. 6 is a flowchart of a health network software according to an embodiment of the present invention.

FIG. 6 is a flowchart that shows the algorithm executed by the health network processor 406. In the health network system 404, the ID request sent by the pulse oximeter 102 is received (step 602). The ID number is matched to value(s) listed in the ID database 410 to identify the module type (step 604). A module program database 412 is then preferably consulted by, for example, the processor 406 to identify the necessary program data files to run the module 104 that transmitted the ID number (step 606). Afterwards, the program data files are sent to the pulse oximeter 102 (step 608).

FIG. 7 is an embodiment of the ID database 410 of the present invention. The ID database 410 comprises two columns for the ID number and the module type. For example, an ID number of "0154873" corresponds to a pulse oximeter with type "TK 427 Pulse Oximeter."

FIG. 8 is an embodiment of the module program database 412. The program module database comprises two columns for the module type and the program data files, for example, data files associated with the module type "BTL-A4 Controller (Bed)" include "BTLmain.dat," "A4DisplayDriver.dat," and "A4GUI.dat." Other data formats may also be used in accordance with embodiments of the present invention.

In another exemplary embodiment of the present invention, a doctor monitors the vital signs of a patient having breathing problems. The doctor selects a number of modules customized to the patient's condition. The doctor may, for example, select a blood pressure (BP) module and a microphone module to connect to a pulse oximeter platform to monitor the patient's BP and respiration. One or more RFID tags residing in the microphone module and BP module transmits RFID tag numbers to the pulse oximeter. The RFID tag number corresponding to the microphone sensor is identified by the pulse oximeter, and thus, the microphone module is operated according to the microphone module driver already stored in the pulse oximeter memory module. However, if the RFID tag number corresponding to the BP module is not recognized by the pulse oximeter, the pulse oximeter connects to the pulse oximeter manufacture's website to determine the identity and compatibility of the newly connected module and download the necessary drivers. Once the BP module driver is downloaded, the BP module can be operated to measure the BP of the patient.

After the acquisition of BP data, audio data, and pulse oximeter data, these data sets are analyzed by the pulse oximeter processor to provide relationships between these data sets and to guide the doctor in making an accurate diagnosis. Following these steps, the doctor may remove the BP sensor and connect a display module to view the processed results.

The present invention is not intended to be restricted to the several exemplary embodiments of the invention described above. Other variations that may be envisioned by those skilled in the art are intended to fall within the disclosure.

The invention claimed is:

1. A modular pulse oximeter platform with interchangeable modules for use with a patient, the modular pulse oximeter platform comprising:
   a pulse oximeter including a power source, a remote communication module for communicating with a health network, a processor, a memory, and an ID reader; and
   a plurality of modules each having an active subunit, another processor, another memory, and an ID transmitter that transmits an ID number that uniquely identifies the respective module, wherein each active subunit is a physiological sensor configured to measure a physiological parameter of the patient, including at least one of a respiration, a pulse, a blood pressure, a temperature, and a pH, of the patient, each of the pulse oximeter and the plurality of modules further comprise one or more connections configured to mechanically, electronically, and electrically connect in a serial manner the pulse oximeter and the plurality of modules, and the connected plurality of modules are customized to a patient, identified by the pulse oximeter, and operated according to predefined operational parameters.

2. The modular pulse oximeter platform with interchangeable modules of claim 1, wherein the one or more connections of each of the plurality of modules further comprises:
one or more mechanical connections configured to mechanically interlock the module to another of the plurality of modules or the pulse oximeter;
a power communication configured to enable a supply of power from the power source to the module; and
a data connection configured to enable a communication of data among the pulse oximeter and the plurality of modules.

3. The modular pulse oximeter platform of claim 2, wherein the pulse oximeter is a portable pulse oximeter device configured to measure an oxygen saturation of the patient, while worn on a patient's finger.

4. The modular pulse oximeter platform of claim 3, wherein the one or more mechanical connections comprise
a first connection located on one side of the modules or the pulse oximeter, and
a second connection located on an opposite side of the module or the pulse oximeter and mechanically interlockable with the first connection.

5. The modular pulse oximeter platform of claim 2, wherein the plurality of modules are selected from the group consisting of a temperature module, a blood pressure module, a microphone module, a GPS module, a security alert module, an ID module, an accelerometer module, a chemical detection module, an SD card module, and a Bluetooth sensor module.

6. The module pulse oximeter platform of claim 2, wherein the health network comprises a health network processor, a communication module, an ID database, and a module program database, wherein the module program database stores in a table form the module types and a number of program data files necessary to operate the module types.

7. The module pulse oximeter platform of claim 6, wherein the ID database comprises one or more ID numbers and one or more module types corresponding to the ID numbers.

8. The module pulse oximeter platform of claim 6, wherein the health network is a cloud service network.

9. The module pulse oximeter platform of claim 2, wherein the ID reader and the ID transmitter are wireless communication modules adapted for RFID, Bluetooth, Wi-Fi, cellular communication, or other wireless communication technology.

10. The module pulse oximeter platform of claim 2, wherein the ID reader and the ID transmitter are functions performed by the processors of the pulse oximeter and the plurality of modules, respectively.

* * * * *